United States Patent [19]

Umehara et al.

[11] 4,436,726
[45] Mar. 13, 1984

[54] N-ACYLPEPTIDE COMPOUND, PROCESSES FOR THE PREPARATION THEREOF AND THE PHARMACEUTICAL COMPOSITIONS

[75] Inventors: Kazuyoshi Umehara, Ashiya; Hirokazu Tanaka, Takarazuka; Itsuo Uchida, Kyoto; Masanobu Kohsaka, Sakai; Hiroshi Imanaka, Mishima, all of Japan

[73] Assignee: Fujisawa Pharmaceutical Co., Ltd., Osaka, Japan

[21] Appl. No.: 329,075

[22] Filed: Dec. 9, 1981

[30] Foreign Application Priority Data

Dec. 15, 1980 [GB] United Kingdom ............... 8040130

[51] Int. Cl.³ .................. C07C 103/52; A61K 37/02; C07C 67/02
[52] U.S. Cl. ........................ 424/177; 260/112.5 R; 560/253; 560/251
[58] Field of Search ............... 260/112.5 R; 424/177; 560/253, 251

[56] References Cited

U.S. PATENT DOCUMENTS 3,538,070 11/1970 Geiger et al. ............... 260/112.5 R
4,205,069 5/1980 Beluzzi et al. ............... 260/112.5 R
4,221,675 9/1980 Schermann et al. ............... 560/253

FOREIGN PATENT DOCUMENTS 11283 11/1979 European Pat. Off. ..... 260/112.5 R
2053232 6/1980 United Kingdom .

OTHER PUBLICATIONS

I. Yano et al., Occurrence of 2- and 3-Hydroxy Fatty Acids in High Concentrations in the Extractable and Bound Lipids of Flavobacterium Meningosepticum and Flavobacterium IIb, *Chemical Abstracts*, vol. 85, No. 21, Abstract No. 156243x, p. 241, (Nov. 22, 1976).

S. Kusumoto et al., Synthesis of Long Chain Fatty Acid Esters of N-acetylmuramyl-L-Alanyl-D-Isoglutamine in Relation to Antitumor Activity, *Tetrahedron Letters*, No. 49, pp. 4899–4902 (1978).

Yasutaka Tahara, Masaru Kameda, Yuzo Yamada and Keiji Kondo, Agricultural and Biological Chemistry, 40 (1), 243–244, 1976.

Primary Examiner—Delbert R. Phillips
Assistant Examiner—F. T. Moezie
Attorney, Agent, or Firm—Oblon, Fisher, Spivak, McClelland & Maier

[57] ABSTRACT

This invention relates to new N-acylpeptide compounds of immunological activity, said compounds being of the formula:

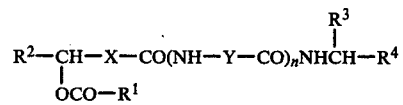

wherein
$R^1$ and $R^2$ are each alkyl or alkenyl;
$R^3$ is hydrogen, lower alkyl, hydroxy(lower)alkyl, heterocyclic(lower)alkyl or ar(lower)alkyl, wherein the aryl moiety may have hydroxy or protected hydroxy;
$R^4$ is carboxy, esterified carboxy, carboxy(lower)alkyl or esterified carboxy(lower)alkyl;
X is bond or lower alkylene;
Y is lower alkylene or lower alkylidene; and
n is an integer of 0 to 1;
or its pharmaceutically acceptable salt.

6 Claims, No Drawings

N-ACYLPEPTIDE COMPOUND, PROCESSES FOR THE PREPARATION THEREOF AND THE PHARMACEUTICAL COMPOSITIONS

This invention relates to a new N-acylpeptide compound and its pharmaceutically acceptable salt.

More particularly, this invention relates to a new N-acylpeptide compound and its pharmaceutically acceptable salt, which have pharmacological activities, to processes for the preparation, and to a pharmaceutical composition comprising the same.

The object N-acylpeptide compound is novel and can be represented by the following formula:

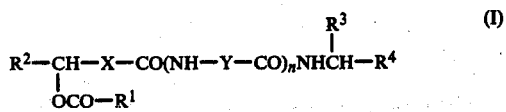

in which
$R^1$ and $R^2$ are each alkyl or alkenyl;
$R^3$ is hydrogen, lower alkyl, hydroxy(lower)alkyl, heterocyclic(lower)alkyl or ar(lower)alkyl, wherein the aryl moiety may have hydroxy or protected hydroxy;
$R^4$ is carboxy, esterified carboxy, carboxy(lower)alkyl or esterified carboxy(lower)alkyl;
X is bond or lower alkylene;
Y is lower alkylene or lower alkylidene and
n is an integer of 0 or 1.

In the above and subsequent description of this specification, suitable examples and illustrations for the various definitions to be included within the scope of this invention are explained in details as follows.

The term "lower" is intended to mean a group having 1 to 6 carbon atom(s), unless otherwise provided.

Suitable "alkyl" for $R^1$ and $R^2$ may include straight and branched ones having 1 to 20 carbon atoms, such as methyl, ethyl, propyl, isopropyl, butyl, isobutyl, tert-butyl, pentyl, isopentyl, hexyl, isohexyl, heptyl, 5-methylhexyl, octyl, 6-methylheptyl, nonyl, 7-methyloctyl, decyl, 8-methylnonyl, undecyl, 9-methyldecyl, dodecyl, 10-methyldecyl, tridecyl, 11-methyldodecyl, tetradecyl, 12-methyltridecyl, pentadecyl, 13-methyltetradecyl, eicosyl or the like, in which the preferred one is C3–C15 alkyl.

Suitable "alkenyl" for $R^1$ and $R^2$ may include straight and branched one having 2 to 20 carbon atoms, such as vinyl, propenyl, 12-methyl-3-tridecenyl, 8-heptadecenyl or the like, in which the preferred one is C14–C17 alkenyl.

Suitable "lower alkyl" moiety in the hydroxy(lower)alkyl for $R^3$ may include lower alkyl having 1 to 6 carbon atom(s), in which the preferred one is C1–C3 alkyl, and suitable hydroxy(lower)alkyl may be hydroxymethyl, 1-hydroxyethyl, 2-hydroxyethyl, 3-hydroxypropyl or the like.

Suitable "heterocyclic(lower)alkyl" for $R^3$ may be 5 to 6 membered heterocyclic(lower)alkyl containing at least one hetero atom such as nitrogen, in which the preferred one is imidazolyl(lower)alkyl (e.g. imidazolylmethyl, imidazolylethyl, etc.) and unsaturated condensed heterocyclic(lower)alkyl containing at least one hetero atom such as nitrogen, in which the preferred one is indolyl(lower)alkyl (e.g. indolylmethyl, indolylethyl, etc.).

Suitable "ar(lower)alkyl" for $R^3$ may include phenyl(lower)alkyl such as benzyl, phenethyl and the like, wherein the aryl moiety such as phenyl may have hydroxy or protected hydroxy.

Suitable "hydroxy protective group" in "protected hydroxy" as the substituent on the above ar(lower)alkyl for $R^3$ may include a conventional hydroxy protective group, for example, ar(lower)alkyl (e.g. benzyl, phenethyl, trityl, etc.), lower alkyl (e.g. methyl, ethyl, propyl or isopropyl, etc.), lower alkenyl (e.g. allyl, etc.), aryl (e.g. phenyl, tolyl, xylyl or naphtyl), tetrahydropyranyl, methoxymethyl and the like.

Suitable "lower alkylene" for X and Y may include methylene, ethylene, trimethylene, tetramethylene and the like, in which the preferred one is C1–C4 alkylene.

Suitable "lower alkylidene" for Y may include ethylidene, propylidene, isobutylidene, butylidene and the like, in which the preferred one is C2–C4 alkylidene.

Suitable "esterified carboxy" or "esterified carboxy moiety" in "esterified carboxy(lower)alkyl" for $R^4$ and $R^{4b}$ may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.), and the like.

Suitable "lower alkyl" for $R^5$ and "lower alkyl moiety" in "carboxy(lower)alkyl" and "esterified carboxy(lower)alkyl" for $R^4$, $R^{4a}$ and $R^{4b}$ may include methyl, ethyl, propyl, isopropyl, butyl, isobutyl, tert-butyl, pentyl, hexyl and the like.

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like.

The N-acylpeptide compound (I) of this invention can be prepared by chemical synthesis and some of said object compounds can also be prepared by fermentation.

Detailed explanation for processes for the preparation of N-acylpeptide compound (I) is made in the following:

I. Synthesis:

(1) Process 1:

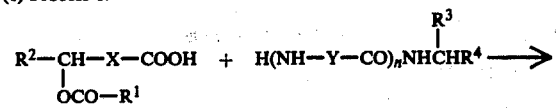

or its reactive derivative at the carboxy group or a salt thereof or its reactive derivative at the amino group or a salt thereof -continued

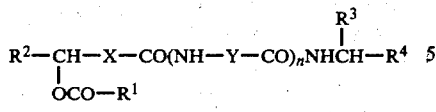

(I)

or a salt thereof (2) Process 2:

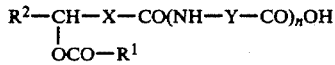

(IIa)

or its reactive
derivative at the carboxy group
or a salt thereof

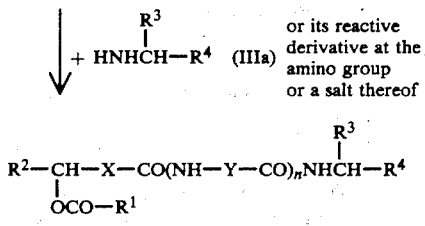

(I)

or a salt thereof (3) Process 3:

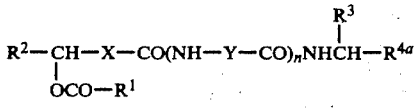

(Ia)

or its reactive
derivative at the carboxy group
or a salt thereof

| esterification of the
↓ carboxy group in $R^{4a}$ $$R^2-CH-X-CO(NH-Y-CO)_nNHCH-R^{4b}$$
$$\quad\quad |\quad\quad\quad\quad\quad\quad\quad\quad\quad\quad\quad\quad |$$
$$\quad OCO-R^1\quad\quad\quad\quad\quad\quad R^3$$

(Ib)

or a salt thereof (4) Process 4:

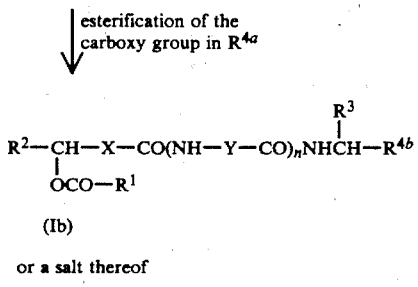

(Ic)

or a salt thereof

| Removal of the hydroxy
↓ protective group in $R^{3a}$

-continued

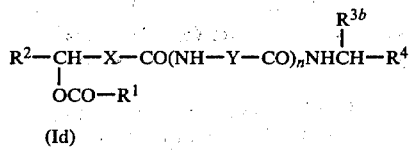

(Id)

or a salt thereof wherein
$R^1$, $R^2$, $R^3$, $R^4$, n, X and Y are each as defined above,
and
$R^{4a}$ is carboxy or carboxy(lower)alkyl,
$R^{4b}$ is esterified carboxy or esterified carboxy(lower)alkyl,
$R^{3a}$ is protected hydroxy substituted ar(lower)alkyl, and
$R^{3b}$ is hydroxy substituted ar(lower)alkyl.

The processes 1 to 4 for the preparation of the object N-acylpeptide compound (I) of the present invention are exaplained in detail in the following.

(1) Process 1:

The compound (I) or a salt thereof can be prepared by reacting the compound (II) or its reactive derivative at the carboxy group or a salt thereof with the compound (III) or its reactive derivative at the amino group or a salt thereof.

Suitable salt of the starting compound (II) may include the same salt with a base as illustrated for the compound (I), and suitable salt of the starting compound (III) may include the same one as illustrated for the compound (I).

Suitable reactive derivative at the carboxy group of the compound (II) may include, for example, an acid halide, an acid anhydride, an activated ester, and the like, and preferably an ester with a N-hydroxy compound such as N-hydroxysuccinimide, N-hydroxyphthalimide, 1-hydroxybenzotriazole, 1-hydroxy-6-chlorobenzotriazole, etc.), and the like.

Suitable reactive derivative at the amino group of the compound (III) may include a conventional one, for example, a silyl derivative formed by the reaction of the compound (III) with a silyl compound such as bis(-trimethylsilyl)acetamide or trimethylsilylacetamide, and the like.

The suitable reactive derivatives of the compound (II) or (III) can optionally be selected from the above according to the kinds of the compounds (II) or (III) to be used practically.

This reaction can be carried out in the presence of an organic or inorganic base such as alkali metal (e.g. lithium, sodium, potassium etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, and the like.

In case that the compound (II) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to a so-called "Vilsmeier reagent") formed by the reaction of an amide compound such as N,N-di(lower)alkylformamide (e.g. dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphoshoramide, etc., or a mixture thereof.

Among these solvents, hydrophilic solvents may be used in a mixture with water.

The reaction temperature is not critical and the reaction is usually carried out under cooling to warming.

(2) Process 2:

The compound (I) or a salt thereof can also be prepared by reacting the compound (IIa) or its reactive derivative at the carboxy group or a salt thereof with the compound (IIIa) or its reactive derivative at the amino group or a salt thereof.

Suitable salt of the starting compound (IIa) may include the same salt with a base as illustrated for the compound (I), and suitable salt of the starting compound (IIIa) may include the same one as illustrated for the compound (I).

Suitable reactive derivative at the carboxy group of the compound (IIa) and suitable reactive derivative at the amino group of the compound (IIIa) may be the same ones as exemplified in the Process 1.

This reaction can be carried out according to the same manner to that of Process 1.

(3) Process 3:

The compound (Ib) or a salt thereof can be prepared by subjecting the compound (Ia) or its reactive derivative at the carboxy group or a salt thereof, to esterification reaction.

The esterification can be conducted by reacting a compound (Ia) or its reactive derivative at the carboxy or a salt thereof with a conventional esterifying agent.

The preferred reactive derivative at the carboxy group of the compound (Ia) can be referred to that of the compound (II) as exemplified in the Process 1.

Suitable esterifying agent may include lower alkanol (methanol, ethanol, propanol, etc.), diazoalkane (e.g.

diazomethane, diazoethane, diazopropane, etc.), and the like.

The reaction can be carried out in the presence of a solvent such as methanol, ethanol, propanol, etc. within a temperature range of cooling to warming.

(4) Process 4:

The compound (Id) or a salt thereof can be prepared by subjecting compound (Ic) a salt thereof to a removal reaction of hydroxy protective group.

Suitable example of a salt of compound (Ic) may include the same one as illustrated for the compound (I). This reaction is carried out by a conventional method, such as hydrolysis or catalytic reduction.

The hydrolysis is usually carried out by treating the compound (Ic) or its salt with water probably in the presence of an acid such as hydrobromic acid, hydrochloric acid, formic acid, acetic acid, trifluoroacetic acid or the like. The hydrolysis can be also carried out in a solvent such as a hydrophilic organic solvent.

The catalytic reduction usually carried out according to a conventional manner known in the arts in the presence of a conventional catalyst such as palladium black or the like in a conventional solvent such as water, methanol, ethanol, propanol, N,N-dimethylformamide, or a mixture thereof.

The reaction temperature of this reaction is not critical and the reaction is usually carried out under cooling to warming.

However, it is to be understood that the reaction condition for removing the protective groups may vary depending upon a kind of the protective groups to be used.

The starting compound (II) to be used in this process is novel and can be prepared by the following process:

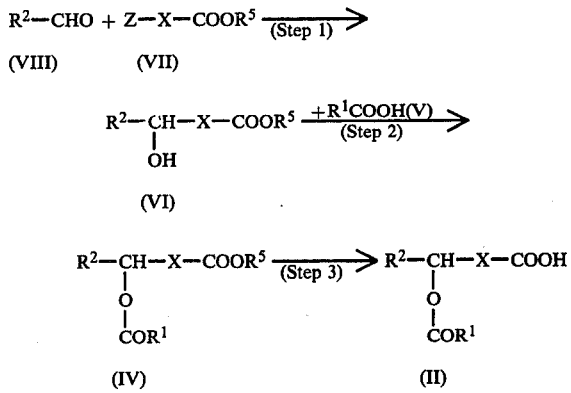

wherein
R$^1$, R$^2$ and X are each as defined above,
Z$_5$ is halogen (i.e., chlorine, bromine, or iodine) and R$^5$ is lower alkyl.

(1) Step 1:

This reaction can carried out in accordance with so called Reformatsky reaction. Namely, this reaction can be carried out by reacting the compound (VIII) with the compound (VII) in the presence of metal such as zinc, magnesium, lithium, aluminum, cadmium or the like. The reaction may be carried out preferably in the presence of iodine.

This reaction may be usually carried out in a solvent such as benzene, ether, tetrahydrofuran, etc. or the mixture thereof at ambient temperature or under heating.

(2) Step 2:

The compound (IV) is prepared by acylating a hydroxy group of the compound (VI) with the carboxylic acid (V) or its reactive derivative at the carboxy group.

The reactive derivative may include an acid halide, an acid anhydride, an activated ester and the like.

The reaction is conducted in a conventional solvent such as pyridine, etc. uneder cooling to heating.

(3) Step 3:

The compound (II) or its salt can be prepared by hydrolysing the compound (IV).

The method of hydrolysis includes a conventional one using an organic or inorganic acid such as formic acid, trifluoroacetic acid, benzenesulfonic acid, hydrochloric acid, or the like. The reaction is conducted in the presence or absence of a solvent at the ambient temperature or under warming.

II Production by Fermentation

Among the object compounds of this invention, some specific compounds were found to be also produced by fermentation. And, said specific compounds can be represented by the following formula (I') and the salt thereof.

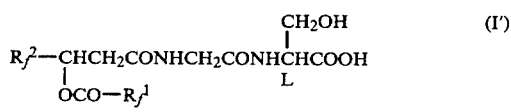

in which, $R_f^1$ is 12-methyl-3-tridecenyl and
$R_f^2$ is 11-methyldodecylor 12-methyltridecyl, or
$R_f^1$ is 12-methyltridecyl and
$R_f^2$ is 11-methyldodecyl or 12-methyltridecyl.

Each specific compound included in the compounds (I') can be represented as follows.

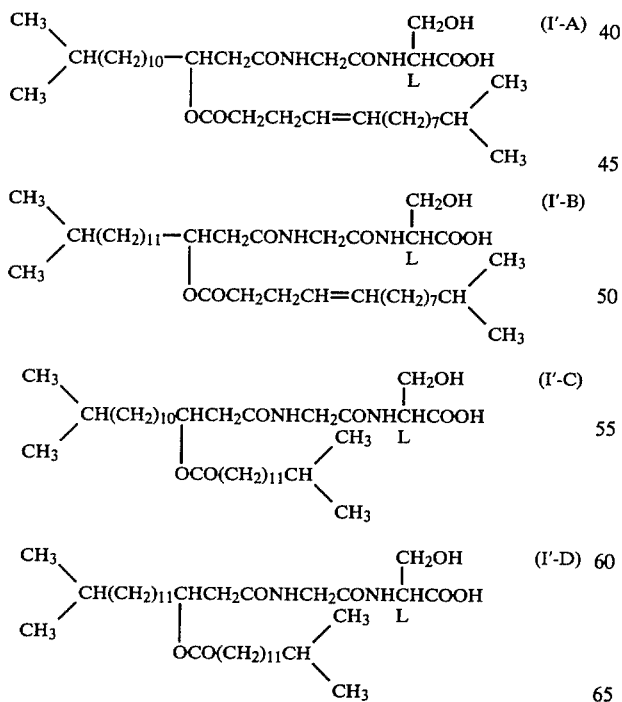

The compound (I') as defined above, i.e. specifically compound (I'-A), compound (I'-B), compound (I'-C) and compound (I'-D), can be produced by culturing a microorganism belonging to the genus Flavobacterium in a conventional manner.

(1) Re. Microorganism:

The microorganism which can be used for the production of the compound (I') is a strain belonging to the genus Flavobacterium, more particularly Flavobacterium sp. No. 3559 newly isolated from Iriomotejima, Okinawa Prefecture, Japan.

A culture of the living organism of Flavobacterium sp. No. 3559 has been deposited to a permanent stock culture collection of the American Type Culture Collection, under ATCC No. 31701.

It is to be understood that the production of the compounds(I') is not limited to the use of the particular organism described herein, which is given only for illustrative purpose. That is, an artificial as well as natural mutants can also be used for the production of the compounds(I'). Such an artificial mutant is produced from the microorganism described herein by conventionl means, such as physical treatment (e.g. X-rays, ultra-violet radiation etc.), treament with chemicals (e.g. N-methyl-N'-nitro-N-nitrosoguanidine, 2-aminopurine, nitrogen mustard oils etc.) or the like.

Flavobacterium sp. No. 3559 (ATCC 31701) has the following morphological and physiological characteristics. For the characterization of the strain ATCC 31701, the procedures described in Bergey's Manual of Determinative Bacteriology (8th Edition) were followed.

(1) Morphological characteristics

Morphological observation of the strain ATCC 31701 was carried out by both optical and electron microscopy with cells cultured mainly on nutrient agar for 24 hours at room temperature.

The following results were obtained.

The organism is non-sporulating, non-motile and Gram-negative.

The cell shape is rod with rounded ends and sizes of the cells are in the range of 0.5×1.5—2.5 μm.

(2) Physiological characteristics

Physiological characteristics of the strain are summarized in Table 1 and 2.

TABLE 1

| Test | Response |
|---|---|
| Oxidase reaction | Positive |
| Catalase reaction | Positive |
| Carbohydrate metabolism (O/F medium) | Fermentative |
| Change of pH in milk | Slightly acidified |
| Milk peptonization | Slow peptonization |
| Milk coagulation | Negative |
| Gelatin liquefaction | Slow liquefaction |
| VOGES-PROSKAUER reaction | Negative |
| Indole production in peptone broth | Negative |
| H2S production | Negative |
| Nitrates reduced to nitrites | Negative |
| Temperature range for growth | 8-33° C. |
| Optimum temperature for growth | 25-27° C. |
| pH range for growth | 6-8 |
| Optimum pH for growth | 7 |
| Energy metabolism | Aerobic |
| Growth in 2% NaCl | Negative |
| Growth on citrate medium | Negative |
| Growth on sodium acetate medium | Negative |
| Urease reaction | Negative |
| Glucose oxidase test | Negative |
| Growth on ammonium ion and glucose as sole sources of nitrogen and carbon | Negative |
| Growth on arginine as a sole carbon source of nitrogen and carbon | Negative |
| Growth on ornithine as a sole carbon source of nitrogen and carbon | Negative |

TABLE 1-continued

| Test | Response |
| --- | --- |
| Growth on lysine as a sole carbon source of nitrogen and carbon | Negative |
| G + C content of DNA | 34–37 mole % |

TABLE 2

| Cleavage of carbohydrate by the strain ATCC 31701. | | |
| --- | --- | --- |
| Carbon source | Acid formation | Gas formation |
| Glucose | + | − |
| Maltose | ± | − |
| Sucrose | − | − |
| Salicin | − | − |
| Sorbitol | − | − |
| Mannitol | − | − |
| Lactose | − | − |
| Inositol | − | − |
| Fructose | ± | − |
| Xylose | − | − |
| Arabinose | − | − |
| Starch | − | − |
| Glycerin | − | − |
| Galactose | − | − |
| Mannose | − | − |

Note:
+, good formation
±, probable formation
−, no formation (3) Taxonomy

According to Bergey's Manual of Determinative Bacteriology, the strain ATCC 31701 was considered to belong to genus Flavobacterium from those characteristics as described above.

(2) Re. Fermentation

Fermentation for production of the compounds (I') is conducted by culturing a compound (I') producing strain belonging to genus Flavobacterium in a nutrient medium containing assimilable sources of carbon and nitrogen, which is conventionally used for the fermentation of bacteria, preferably under aerobic conditions (e.g. shaking culture, submerged culture, etc.), the detail of which will be apparent in the following.

As suitable carbon and nitrogen sources, there may be exemplified meat extract, peptone, yeast extract and the like.

The fermentation is usually conducted at a temperature of about 20° C. to 40° C., preferably 30° C. for a period of 24 hours to 72 hours.

(3) Re: Isolation

The compounds (I'), i.e.(I'-A), (I'-B), (I'-C) and(I'-D) are all found in cultured cells, and can be separated from the cultured cells by means of an extraction using a solvent such as acetone, ethyl acetate, etc.

The extract is purified by a conventional method used in the isolation of the acid substances, that is, an extraction using a solvent such as ethyl acetate in acidic condition and a column chromatography using silicic acid.

For further purification of the compound (I'), a reverse phase chromatography is preferably employed.

By the above-mentioned purification, the compounds(I'-A), (I'-B), (I'-C) and(I'-D) can be obtained as mixed substances thereof.

For separation of each of the compounds(I'-A), (I'-B), (I'-C) and (I'-D), high pressure liquid chromatography is preferably employed.

The compounds (I') obtained according to the above-mentioned processes have the following physico-chemical properties;

Physico-chemical properties common to the compounds (I'-A), (I'-B), (I'-C) and (I'-D):

(1) Appearance:
A colorless waxy substances
(2) Nature of substance:
Acidic substance
(3) Solubility:
Soluble: methanol, ethanol, chloroform
Sparingly soluble: benzene, hexane
Insoluble: water
(4) Thin layer chromatography:
Layer: Silica gel sheet (Kieselgel 60 F254, made by MERCK & CO., Inc.)

| Developing solvent | Rf value |
| --- | --- |
| Chloroform-methanol(2:1) | 0.25 |
| benzene-dioxane-acetic acid(10:5:1) | 0.30 |

(5) Color reaction:
Positive: each reaction with cerium sulfate and phosphomolybdic acid
Negative: Molisch's reaction, Dragendorff's reaction, Ehrlich's reaction and Ninhydrin reaction Physico-chemical properties of compound (I'-A) per se:

(1) Molecular weight:
638
(calculated from mass-spectrometry of methyl ester thereof)
(2) Molecular formula:
$C_{36}H_{66}N_2O_7$
(3) Elementary analysis (%):
C 67.37; H 10.42; N 4.14.
(4) Melting point:
144°–145° C.
(5) Specific rotation:
$[\alpha]_D^{25°}$ C. +15.3° (C=0.3, chloroform)
(6) ultraviolet absorption spectrum:
$\lambda_{max}^{methanol}$: 207 nm ($\epsilon$=2480)
(7) Infrared absorption spectrum
$\nu_{max}^{chloroform}$: 3350, 2950, 2860, 1725, 1660, 1525, 1475, 1385, 1370, 1230, 1080, 1065 cm$^{-1}$.
(8) Nuclear magnetic resonance absorption spectrum:
δ (ppm) (CDCl$_3$:CD$_3$OD=1:1): 0.85 (12H, d, J=6 Hz), 1.1 to 1.5 (30H, m), 1.60 (4H, m), 2.04 (2H, m), 2.36 (4H, m), 2.55 (2H, d, J=6 Hz), 3.92 (4H, m), 4.53 (1H, m), 5.20 (1H, m), 5.35 (2H, m).

Physico-chemical properties of compound (I'-B) per se:

(1) Molecular weight:
652
(calculated from mass-spectrometry of methyl ester thereof)
(2) Molecular formula:
$C_{37}H_{68}N_2O_7$
(3) Elementary analysis (%)
C 67.95 H 10.43 N 4.10
(4) Melting point:
126°–127° C.
(5) Specific rotation:
$[\alpha]_D^{22°}$ C. +16.7 (C=0.33, chloroform)
(6) Ultraviolet absorption spectrum:
$\lambda_{max}^{methanol}$: 207 nm ($\epsilon$=2160)
(7) Infrared absorption spectrum:

$\nu_{max}^{chloroform}$: 3350, 2950, 2860, 1730, 1715, 1660, 1525, 1475, 1370, 1220, 1180, 1080 cm$^{-1}$.

(8) Nuclear magnetic resonance absorption spectrum:

δ (ppm) (CDCl$_3$:CD$_3$OD=1:1): 0.85 (12H, d, J=6 Hz), 1.1–1.5 (32H, m), 1.60 (4H, m), 2.04 (2H, m), 2.36 (4H, m), 2.55 (2H,d,J=6 Hz), 3.92 (4H, m), 4.53 (1H, m), 5.20 (1H, m), 5.35 (2H, m).

Physicochemical properties of the compound (I'-C) per se:

(1) Molecular weight:
640 (calculated from mass-spectrometry of methyl ester thereof)

(2) Molecular formula:
C$_{36}$H$_{68}$N$_2$O$_7$ (3) Elementary analysis (%):
C 67.28, H 10.48, N 4.15.

(4) Melting point:
154°–155° C.

(5) Specific rotation:
$[\alpha]_D^{25°\ C.}$+15.9° (C=0.37, chloroform)

(6) Ultraviolet absorption spectrum:
$\lambda_{max}^{methanol}$: 206 nm (ε=1920)

(7) Infrared absorption spectrum:
$\nu_{max}^{chloroform}$: 3350, 2950, 2860, 1725, 1660, 1525, 1475, 1392, 1370, 1230, 1080 cm$^{-1}$.

(8) Nuclear magnetic resonance absorption spectrum:

δ (ppm) (CDCl$_3$:CD$_3$OD=1:1): 0.85 (12H, d, J=6 Hz), 1.1 to 1.5 (38H, m), 1.60 (4H, m), 2.32 (2H, t, J=7 Hz), 2.54 (2H, d, J=6 Hz), 3.92 (4H, m), 4.53 (1H, m), 5.20 (1H, m).

Physico-chemical properties of the compound (I'-D) per se:

(1) Molecular weight:
654 (calculated from mass-spectrometry of methyl ester thereof)

(2) Molecular formula:
C$_{37}$H$_{70}$N$_2$O$_7$ (3) Elementary analysis (%):
C 67.74 H 10.55 N 4.19

(4) Melting point:
137°–138° C.

(5) Specific rotation:
$[\alpha]_D^{22°\ C.}$+19.75° (C=0.8, chloroform)

(6) Ultraviolet absorption spectrum:
$\nu_{max}^{methanol}$: 206 nm (ε=1900)

(7) Infrared absorption spectrum:
$\nu_{max}^{chloroform}$: 3350, 2950, 2870, 1725, 1660, 1520, 1475, 1390, 1370, 1230, 1080 cm$^{-1}$.

(8) Nuclear magnetic resonance absorption

δ (ppm) (CDCl$_3$:CD$_3$OD=1:1) 0.85 (12H, d, J=6 Hz), 1.1 to 1.5 (40H, m), 1.60 (4H, m), 2.32 (2H, t, J=7 Hz), 2.54 (2H, d, J=6 Hz), 3.92 (4H, m), 4.53 (1H, m), 5.20 (1H, m).

As a result of the above physico-chemical properties and further extensive studies, each chemical structure of the compounds(I'-A), (I'-B), (I'-C) and(I'-D) which are produced by the fermantation could be proposed with a firm belief as indicated hereinabove.

Acute toxicity of the compound (I'-D) in ddy mice is above 500 mg/kg by intraperitoneal injection.

As to the object compound (I) which is prepared according to the aforementioned processes, it is to be noted that the compound includes one or more stereoisomers, which is due to the asymmetric carbon atoms in its molecule and all of such isomers are included within the scope of this invention.

The compound (I) of this invention has anticomplementary activity and fibrinolytic activity, and is useful as a therapeutic agent for immune-complex diseases or autoimmune diseases such as nephritis, rheumatic diseases, systemic lupus erythematosus, etc. and thrombosis such as cerebral apoplexy, coronary insufficiency, pulmonary embolism, etc.

Test results on the pharmacological effects of the compound (I) of this invention are shown below.

(1) Anticomplementary activity:

The anticomplementary activity of the test compound was measured according to the test method as described in Experimental Immunochemistry, edited by E. A. Kabat and M. M. Mayer, 2nd ed., Springfield, III: C. C. Thomas (1961) pages 133–240.

A mixture of 1 ml of a 5-fold diluted solution of a Veronal buffer solution containing 1.5×10$^{-4}$M Ca$^{2+}$ and 5×10$^{-4}$M Mg$^{2+}$ and isotonic gelatin, 1.5 ml of complement serum (guinea pig complement) diluted 400 times with a physiological saline solution and 0.05 ml of a solution of a test compound (in this case, a test compound was dissolved in a physiological saline solution) was incubated at 37° C. for 30 minutes. To the said mixture there was added 0.4 ml of sensitized erythrocytes suspension containing 5×10$^8$ cells/ml and said mixture was incubated at 37° C. further for 60 minutes. After the incubation, the mixture was centrifuged in 3,000 rpm at 4° C. for 10 minutes.

The absorbance (OD$_{541}$) of the supernatant separated was measured at 541 nm, and the extent that the test compound inhibited the hemolysis of the sensitized erythrocytes was determined. The 50% hemolysis inhibitory activity value (μg/ml)(IC$_{50}$) measured by the above method is shown in Table 1.

The results are expressed in Table 1 as the concentration of each drugs inhibiting the hemolysis activity by 50% (IC$_{50}$).

TABLE 1

| Test compound (Example No.) | Anticomplementary Activity (IC$_{50}$) (μg/ml) |
|---|---|
| 1 | 1.0 |
| 2 | 0.03–0.04 |
| 3 | 0.12 |
| 4 | 1.1 |
| 7 | 0.02–0.03 |
| 8 | 0.04–0.06 |
| 9 | 0.1 |
| 10 | 0.03–0.04 |
| 11 | 0.36 |
| 12 | 0.59 |
| 13 | 0.72 |
| 14 | 0.23 |
| 15 | 2.8 |
| 16 | 4.2 |
| 18 | 3.2 |
| 19 | 4.0 |
| 20 | 2.8 |
| Compound (I'-A) | 3.0 |
| 21 Compound (I'-B) | 1.0 |
| Compound (I'-C) | 3.0 |
| Compound (I'-D) | 1.0 |
| 26 | 3.5 |
| 27 | 0.44 |
| 29 | 0.59 |
| 32 | 1.32 |
| 34 | 0.02 |
| 35 | 0.03 |
| 36 | 0.08 |
| 38 | 3.4 |
| 43 | 5.11 |

(2) Therapeutic effect of nephrotoxin-type nephritis:
(i) Preparation of anti-rat kidney rabbit serum.

The kidneys of SD male rats weighing about 250–300 g were sufficiently perfused with 0.9% saline. The renal cortical tissue was homogenized with 0.9% saline using a Teflon homogenizer. 4 ml of the homogenate was then suspended into the same volume of Freund's complete adjuvant. 2 ml of the said mixture was given subcutaneously to male rabbits weighing about 3 kg. 4 weeks later, 2 ml of the mixture was given intramuscularly as a booster. At the 5th week, a blood sample was taken. The serum separated by centrifugation at 3,000 rpm for 30 minutes was inactivated by heating at 56° C. for 30 minutes and preserved by freezing until just before use.

(ii) Induction of experimental nephritis (modified type of Masugi nephritis)

Experimental nephritis was induced in groups of 5 male rats weighing about 150–200 g by a single intravenous injection of 1 ml of the anti-kidney serum obtained in the above procedures.

(iii) Evaluation of anti-nephritic effect of drugs.

Drugs were given to a group of 5 rats once a day for 5 consecutive days from the 2nd day before the injection of anti-kidney serum. Each drug was dissolved into 3% sodium bicarbonate solution and given intraperitoneally in a volume of 1 ml/rat. In addition to the above drug-treated nephritic group, the non-treated-nephritic group(control) was set in the experiment. The proteinuria level(total amount excreted into the urine over a 12 hour period) was measured using turbidometry employing bovine serum albumin as a control by means of sulfosalicylic acid.

The results obtained are shown in Table 2.

TABLE 2

| Test Compound (Example No.) | Dose (mg/kg) | protein uria 1st day | level 4th day | (mg/12 hours) 7th day |
|---|---|---|---|---|
| 2 | 30 | 3.5 | 5.5 | 16.5 |
|  | 10 | 5.9 | 3.7 | 39.6 |
| 21[Compound (Id)] | 30 | 4.1 | 1.8 | 22.5 |
| Control | 0 | 10.8 | 15.5 | 39.1 |

These compounds were found to inhibit the primary reaction of nephrotoxin-type nephritis.

(3) Fibrinolytic activity:

The enhancement of the fibrinolytic activity of the test compounds was measured according to the modified diluted whole blood clot lysis time method described in G. R. Fearnley, G. V. Balmforth, E. Fearnley: Clin. Sci. 16, 645–650 (1957)

I. S. Chohan et al: Thrombos. Diathes. Haemorrh. 33, 226 (1975) and

I. M. Nilsson et al: Handbook of Experimental Pharmacology 46, 110

(i) Test method:

Fresh rabbit blood was diluted 20 times with 1/15 M phosphate buffer(pH 7.4). A mixture of 400 μl of the diluted blood solution and 50 μl of a test compound(300 μg/ml) was incubated at 37° C. for 30 minutes. To the mixture were added 50 μl of urokinase solution(100 IU/ml) and 50 μl of bovine thrombin(100 N.I.H. u/ml). The clot produced in tubes was incubated at 37° C. for various periods of time. At the end of each incubation interval (15 minutes interval), 2.5 ml of distilled water was added to lyse erythrocytes released from clotted blood and absorbance($OD_{541}$) of the supernatant separated by centrifugation(3,000 rpm for 10 minutes) from the reaction mixture was measured. The fibrinolytic activity of the test compound was determined by the time in minutes needed for the complete lysis of the blood clot.

(ii) Results:

The test results are shown in Table 3.

In the absence of a test compound, it took more than 2 hours to lyse blood clot in the above condition. However, blood clot was lysed in the presence of test compounds after 15 minutes(symbol: ++) and 45 minutes(-symbol: +) incubation, respectively. Samples which were incapable of lysing blood clot within 1 hour incubation were expressed as symbol (−).

TABLE 3

| Test Compound (Example No.) | Fibrinolytic Activity |
|---|---|
| 9 | + |
| 11 | + |
| 15 | ++ |
| 18 | + |
| 19 | + |
| 20 | + |
| 26 | + |
| 27 | + |
| 32 | ++ |
| 34 | + |
| 35 | + |
| 36 | + |
| 38 | + |
| 43 | + |

The compound (I) of this invention in admixture with pharmaceutically acceptable carriers can be administered to mammals including human being in a form of a pharmaceutical composition such as capsules, tablets, granules, powders, buccal tablets, sublingual tablets, and solutions.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropyl-cellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycolestarch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of grycyrlysine, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. polysolbate 80, emalgen 408 (surface active agent), emasol (surface active agent), etc.], aqueous diluting agent (e.g. water), base wax (e.g. cacao butter, polyethyleneglycol, witepsol, white petrolatum, etc.).

A dosage of the object compounds is to be varied depending on various factors such as kind of diseases, weight and/or age of a patient, and further the kind of administration route.

The following Examples are given for the purpose of illustrating this invention.

PREPARATION 1

(1) Activated zinc (118 mg), a small crystal of iodine, and tetrahydrofuran (3 ml) were stirred and heated under reflux. To the mixture was added a solution of tert-butyl bromoacetate (312 mg) and 13-methyltetradecanal (226 mg) in tetrahydrofuran (3 ml), and the reactants were stirred and heated under reflux for 1 hour. Anhydrous conditions were maintained throughout the experiment. The cooled solution was poured into 0.1 N hydrochloric acid (5.6 ml) and the pH was adjusted to 2.0 with 2 N hydrochloric acid. The excess of zinc was filtered off and the crude products were extracted with ethyl acetate. The ethyl acetate solution was washed with aqueous sodium hydrogen carbonate and brine, and then dried over magnesium sulfate. The ethyl acetate was evaporated off under reduced pressure to give the crude ester, which was purified by column chromatography on silica gel (Merck) and eluted with a mixture of cyclohexane and ethyl acetate (19:1). The fractions containing the object compound were combined and concentrated under reduced pressure. The residue was dried by high vacuum pump to afford an oil of tert-butyl 3-hydroxy-15-methylhexadecanoate (180 mg).

IR (film): 3450, 2920, 2850, 1715 cm$^{-1}$.

NMR (CDCl$_3$, δ): 4.0 (1H, m), 3.0 (1H, d, J=4 Hz), 2.3 to 2.43 (2H, m), 1.5 (9H, s), 1.05 to 2.0 (23H, m), 0.87 (6H, d, J=6 Hz).

(2) Thionyl chloride (1 ml) was added to a solution of 13-methyltetradecanoic acid (250 mg) in dry benzene (3 ml), and the resulting mixture was refluxed for 1 hour. After excess thionyl chloride and benzene were distilled off, the residue was taken up in benzene and the solution was evaporated off under reduced pressure. To the residual acid chloride which was dried by high vacuum pump were added dry pyridine (3 ml) and a solution of tert-butyl 3-hydroxy-15-methylhexadecanoate (69 mg) in pyridine (1 ml). The resulting mixture was heated at 80° C. overnight. The cooled reaction mixture was poured into ice water, and the mixture was stirred for 30 minutes, acidified with 1 N hydrochloric acid, extracted with ethyl acetate, washed with brine and dried over magnesium sulfate. After evaporation of the solvent, the residue was subjected to column chromatography on silica gel (Merck) and eluted with a mixture of hexane and ethyl acetate (97:3). The fractions containing the object compound were combined and concentrated under reduced pressure. The residue was dried up by high vacuum pump to afford an oil of tert-butyl 15-methyl-3-(13-methyltetradecanoyloxy)hexadecanoate (85 mg).

IR (film): 2900, 2820, 1725 cm$^{-1}$.

NMR (CDCl$_3$, δ): 5.2 (1H, m), 2.47 (2H, d, J=6 Hz), 2.2 (2H, t, J=6 Hz), 1.45 (9H, s), 1.1 to 1.9 (44H, m), 0.88 (12H, d, J=6 Hz).

(3) To tert-butyl 15-methyl-3-(13-methyltetradecanoyloxy)hexadecanoate (500 mg) was added trifluoroacetic acid (5 ml) and the mixture was stirred at ambient temperature for 2 hours. Excess trifluoroacetic acid was distilled off under reduced pressure. Dry benzene was added to the residue and the solvent was evaporated off. This operation was repeated three times. The residue was dried up by using high vacuum pump to afford an oil of 15-methyl-3-(13-methyltetradecanoyloxy)hexadecanoic acid (400 mg).

IR (film): 2950, 2850, 1725, 1710 cm$^{-1}$.

NMR (CDCl$_3$, δ): 6.5 (1H, broad s), 5.24 (1H, m), 2.6 (2H, d, J=6 Hz), 2.3 (2H, t, J=7 Hz), 2.0 to 1.0 (44H, m), 0.86 (12H, d, J=6 Hz),

PREPARATION 2

(1) The reaction of hexadecanal (1.2 g) and tertbutyl bromoacetate (1.56 g) was carried out under the presence of activated zinc (0.59 g) according to similar manner to that of Preparation 1-(1) to afford an oil of tert-butyl 3-hydroxyoctadecanoate.

IR (Nujol): 3430, 2910, 2840, 1720 cm$^{-1}$. NMR (CDCl$_3$, δ): 4.0 (1H, m), 3.3 (1H, d, J=4 Hz), 2.32 to 2.44 (2H, m), 1.48 (9H, s), 1.22 to 1.73 (28H, m), 0.9 (3H, t, J=6 Hz).

(2) tert-Butyl 3-hydroxyoctadecanoate (1.068 g) was acylated by the acid chloride derived from hexadecanoic acid (3.84 g) according to similar manner to that of Preparation 1-(2) to give an oil of tert-butyl 3-hexadecanoyloxyoctadecanoate (1.72 g).

IR (film): 2910, 2850, 1730 cm$^{-1}$. NMR (CDCl$_3$), 5.25 (1H, m), 2.48 (2H, d, J=7 Hz), 2.2 (2H, t, J=6 Hz), 1.47 (9H, s), 1.1 to 1.95 (54H, m), 0.9 (6H, t, J=6 Hz).

(3) An oil of 3-hexadecanoyloxyoctadecanoic acid (1.12 g) was obtained fom tert-butyl 3-hexadecanoyloxyoctadecanoate (1.5 g) according to similar manner to that of Preparation 1-(3).

IR (CHCl$_3$): 2920, 2850, 1720 cm$^{-1}$.

NMR (CDCl$_3$, δ): 5.2 (1H, m), 2.58 (2H, d, J=6 Hz), 2.3 (2H, t, J=7 Hz), 1.9 to 1.0 (54H, m), 0.88 (6H, t, J=6 Hz).

PREPARATION 3

(1) The reaction of dodecanal (0.92 g) and tert-butyl bromoacetate (1.56 g) was carried out under the presence of zinc (0.59 g) according to similar manner to that of Preparation 1-(1) to afford an oil of tert-butyl 3-hydroxytetradecanoate (1.21 g).

IR (CHCl$_3$): 3530, 2940, 2860, 1710 cm$^{-1}$.

NMR (CDCl$_3$, δ): 3.9 (1H, m), 3.02 (1H, d, J=3 Hz), 2.28 to 2.40 (2H, m), 1.48 (9H, s), 1.0 to 1.8 (20H, m), 0.9 (3H, t, J=6 Hz).

(2) tert-Butyl 3-hydroxytetradecanoate (314 mg) was acylated by the acid chloride derived from dodecanoic acid (1 g) according to similar manner to that of Preparation 1-(2) to afford tert-butyl 3-dodecanoyloxytetradecanoate (450 mg).

IR (film): 2930, 2850, 1735 cm$^{-1}$.

NMR (CDCl$_3$, δ): 5.24 (1H, m), 2.46 (2H, d, J=6 Hz), 2.28 (2H, t, J=7 Hz), 1.44 (9 H, s), 1.0 to 1.8 (38H, m), 0.88 (6H, t, J=6 Hz).

PREPARATION 4

(1) The reaction of hexanal (720 mg) and tert-butyl bromoacetate (2.265 g) was carried out under the presence of zinc (850 mg) according to similar manner to that of Preparation 1-(1) to afford an oil of tert-butyl 3-hydroxyoctanoate (1.2 g).

IR (CHCl$_3$): 3520, 2940, 2870, 1710 cm$^{-1}$.

NMR (CDCl$_3$, δ): 3.9 (1H, m), 3.02 (1H, d, J=4 Hz), 2.28 to 2.40 (2H, m), 1.46 (9H, s), 1.0 to 1.85 (8H, m), 0.88 (3H, t, J=6 Hz).

(2) Hexadecanoic acid (1.92 g) and tert-butyl 3-hydroxyoctanoate (324 mg) was reacted to afford an oil of tert-butyl 3-hexadecanoyloxyoctanoate (620 mg in the similar method to that of Preparation 1-(2).

IR (CHCl$_3$): 2920, 2850, 1715 cm$^{-1}$.

NMR (CDCl$_3$, δ): 5.2 (1H, m), 2.44 (2H, d, J=7 Hz), 2.26 (2H, t, J=7 Hz), 1.44 (9H, s), 1.0 to 1.9 (34H, m), 0.88 (6H, t, J=6 Hz).

Preparation 5 tert-Butyl 3-hydroxyoctanoate (324 mg) was dissolved in pyridine (10 ml) and hexanoic anhydride (1.6 g) was added thereto. The resulting mixture was heated at 80° C. for 5 hours. To the cooled solution was added water and the mixture was stirred for 30 minutes, and then poured into water. The mixture was acidified with 1 N hydrochloric acid, extracted with ethyl acetate, washed with saturated, aqueous sodium hydrogen carbonate solution and brine, and then dried over magnesium sulfate. Evaporation of ethyl acetate gave a residue, which was purified by column chromatography on silica gel (Merck), and eluted with a mixture of cyclohexane and ethyl acetate (50:1). The fractions containing the object compound were combined and concentrated, and the residue was dried by high vacuum pump to afford an oil of tert-butyl 3-hexanoyloxyoctanoate (457 mg).

IR (CHCl$_3$): 2950, 2860, 1720 cm$^{-1}$.

NMR (CDCl$_3$, δ): 5.2 (1H, m), 2.46 (2H, d, J=6 Hz), 2.27 (2H, t, J=7 Hz), 1.45 (9H, s), 1.0 to 1.85 (14H, m), 0.88 (6H, t, J=6 Hz).

Preparation 6

(1) To a solution of tert-butyl 3-hydroxyhexanoate (300 mg) in pyridine (5 ml) was added n-butyric anhydride (2 ml), and the resulting solution was heated at 100° C. for 2 hours and then allowed to stand overnight. The reaction mixture was diluted with ethyl acetate and washed with diluted hydrochloride aqueous solution and water. Ethyl acetate was distilled off to give a residue which was dissolved in saturated sodium hydrogen carbonate aqueous solution (20 ml) and then methanol (5 ml) was added. After the resulting mixture was stirred at ambient temperature for 2 hours, it was extracted with ethyl acetate, washed with water, and dried over magnesium sulfate. Evaporation of ethyl acetate gave a residue which was dried by high vacuum pump to afford an oil of tert-butyl 3-butanoyloxyhexanoate (368 mg).

NMR (CDCl$_3$, δ): 5.25 (1H, m), 2.47 (2H, d, J=6 Hz), 2.3 (2H, t, J=7 Hz), 1.9 to 1.4 (6H, m), 1.45 (9H, s), 0.95 (6H, t, J=6 Hz).

(2) 3-Butanoyloxyhexanoic acid (250 mg) was obtained from tert-butyl 3-butanoyloxyhexanoate (320 mg) according to similar manner to that of Preparation 1-(3).

IR (CHCl$_3$): 2925, 2850, 1710 cm$^{-1}$.

NMR (CDCl$_3$, δ): 9.1 (1H, s), 5.25 (1H, m), 2.63 (2H, d, J=6 Hz), 2.33 (2H, t, J=7 Hz), 2.0 to 1.2 (6H, m), 0.94 (6H, t, J=6 Hz).

Preparation 7

α-Hydroxypalmiticacid (3.2 g) was dissolved in pridine (15 ml), and palmitoyl chloride (3.3 g) was added thereto under stirring at 0° C. The resulting mixture was allowed to stand over night at room temperature. The reaction mixtue was poured into water and the aqueous solution was stirred at room temperature for 1 hour, followed by acidification with 1 N hydrochloric acid solution, and extraction with ethyl acetate. The extract was washed with water, dried over magnesium sulfate and concentrated to give a residue which was recrystallized from petroleum ether to afford crystals of 2-hexadecanoyloxyhexadecanoic acid (5.4 g). M.p. 55° to 56° C.

IR (CHCl$_3$): 2940, 2860, 1720 cm$^{-1}$.

NMR (CDCl$_3$, δ): 5.1 (1H, m), 2.4 (2H, m), 2.1 to 1.1 (52H, m), 0.95 (6H, t, J=6 Hz).

Preparation 8

(1) Starting from 9-octadecenoyl chloride (15 g) and 2,2-dimethyl-1,3-dioxane-4,6-dione (8 g), 5-(1-hydroxy-9-octadecenylidene)-2,2-dimethyl-1,3-dioxane-4,6-dione (18 g) was obtained as oil according to a similar manner to that of Preparation A-2(1).

(2) Starting from 5-(1-hydroxy-9-octadecenylidene)-2,2-dimethyl-1,3-dioxane-4,6-dione (18 g) and tert-butyl alcohol (200 ml), tert-butyl 3-oxo-11-eicosenoate was obtained as an oil according to a similar manner to that of Preparation A-2(2).

(3) Starting from tert-butyl 3-oxo-11-eicosenoate (13 g), tert-butyl 3-hydroxy-11-eicosenoate (11.76 g) was obtained as a colorless oil according to a similar manner to that of Preparation A-2(3).

IR (CHCl$_3$): 3530, 2940, 2860, 1710 cm$^{-1}$.

NMR (CDCl$_3$, δ): 5.4 (2H, m), 3.9 (1H, m), 3.03 (1H, d, J=4 Hz), 2.4 (2H, d, J=6 Hz), 2.0 (4H, m), 1.5 (9H, s), 1.7 to 1.1 (24H, m), 0.85 (3H, t, J=6 Hz).

(4) Starting from tert-butyl 3-hydroxy-11-eicosenoate (11 g) and 9-octadecenoyl chloride (15 g), tert-butyl 3-(9-octadecenoyloxy)-11-eicosenoate (14 g) was obtained as an oil according to a similar manner to that of Preparation A-2(4).

IR (CHCl$_3$): 2950, 2880, 1725 cm$^{-1}$.

NMR (CDCl$_3$, δ): 5.4 to 5.1 (5H, m), 2.5 (2H, d, J=7 Hz), 2.4 to 1.8 (10H, m), 1.8 to 1.1 (46H, m), 1.45 (9H, s), 0.85 (6H, t, J=7).

(5) Starting from tert-butyl 3-(9-octadecenoyloxy)-11-eicosenoate (14 g), 3-(9-octadecenoyloxy)-11-eicosenoic acid (10.2 g) was obtained as powders according to a similar manner to that of Preparation A-2(5).

IR (CHCl$_3$): 2950, 2880, 1725 cm$^{-1}$.

NMR (CDCl$_3$, δ): 9.7 (1H, s), 5.5 to 5.0 (5H, m), 2.6 (2H, d, J=7 Hz), 2.9 to 1.8 (10H, m), 1.9 to 1.0 (46H, m), 0.85 (6H, t, J=6 Hz).

EXAMPLE 1

To tert-butyl 15-methyl-3-(13-methyltetradecanoyloxy)hexadecanoate (65 mg) prepared by the method described in Preparation 1-(2) was added trifluoroacetic acid (1 ml) and the mixture was stirred at ambient temperature for 1 hour. Excess trifluoroacetic acid was distilled off under reduced pressure. Dry benzene was added to the residue and the solvent was evaporated off. This operation was repeated three times. After drying up completely by using high vacuum pump, the residue (15-methyl-3-(13-methyltetradecanoyloxy)hexadecanoic acid) was dissolved in dioxane (2 ml) and N-hydroxysuccinimide (14 mg) was added. To the stirred mixture was added N,N'-dicyclohexylcarbodiimide (24 mg) at 0° C. The resulting mixture was reached to room temperature and stirred at ambient temperature overnight. The reaction mixture was filtered to remove urea and the filtrate was concentrated. The residue was dissolved in N,N-dimethylformamide (2 ml). The solution was added to a solution of N-glycyl-L-serine (93 mg) and triethylamine (0.08 ml) in water (2 ml). The resulting mixture was stirred at ambient temperature for 8 hours. The reaction mixture was acidified with 1 N hydrochloric acid, extracted with ethyl acetate, washed with brine and dried over magnesium sulfate. Ethyl acetate was evaporated off to give crude products which were subjected to column chromatography on silica gel (Merck) and eluted with mixture of chloroform and methanol (5:1). The fractions containing the object compound were combined and concentrated under reduced pressure. The residue was dried up by high vacuum pump to afford a wax of N-[N-[15-methyl-3-(13-methyltetradecanoyloxy)hexadecanoyl]glycyl]-L-serine (40 mg).

IR (CHCl$_3$): 3350, 2950, 2870, 1725, 1660, 1520, 1475 cm$^{-1}$.

NMR (CDCl$_3$: CD$_3$OD=1:1, δ): 5.20 (1H, m), 4.53 (1H, m), 3.9 (4H, m), 2.54 (2H, d, J=6 Hz), 2.34 (2H, t, J=7 Hz), 1.0 to 1.8 (44H, m), 0.85 (12H, d, J=6 Hz).

EXAMPLE 2

To tert-butyl 3-hexadecanoyloxyoctadecanoate (206 mg) prepared by the method described in Preparation 2-(2) was added trifluoroacetic acid (3 ml) and the mixture was stirred at ambient temperature for 1 hour. Excess trifluoroacetic acid was distilled off under reduced pressure. Dry benzene was added to the residue and the solvent was evaporated off. This operation was repeated three times. After drying up completely by using high vacuum pump, the residue (3-hexadecanoyloxyoctadecanoic acid) was dissolved in dioxane (3 ml) and N-hydroxysuccinimide (35 mg) was added. To the stirred mixture was added N,N'-dicyclohexylcarbodiimide (69 mg) at 0° C. The resulting mixture was reached at room temperature and stirred at ambient temperature overnight. The reaction mixture was filtered to remove N,N'-dicyclohexyl urea and the filtrate was concentrated. The residue was dissolved in N,N-dimethylformamide (2 ml). The solution was added to a solution of N-glycyl-L-serine (280 mg) and triethylamine (0.24 ml) in water (2 ml). The resulting mixture was stirred at ambinet temperature for 8 hours. The reaction mixture was acidified with 1 N hydrochloric acid, extracted with ethyl acetate, washed with brine and dried over magnesium sulfate. Ethyl acetate was evaporated off to give crude products which were subjected to column chromatography on silica gel (Merck) and eluted with a mixture of chloroform and methanol (5:1). The fractions containing the object compound were combined and concentrated undre reduced pressure. The residue was dried up by high vacuum pump to afford an amorphous powder of N-[N-(3-hexadecanoyloxyoctadecanoyl)glycyl]-L-serine (120 mg).

IR (CHCl$_3$): 3350, 2950, 2880, 1720, 1650 cm$^{-1}$.

NMR (CDCl$_3$-CD$_3$OD=1:1, δ): 5.3 (1H, m), 4.57 (1H, m), 3.8 to 4.0 (4H, m), 2.55 (2H, d, J=6 Hz), 2.31 (2H, t, J=6 Hz), 1.1 to 1.9 (54H, m), 0.9 (6H, t, J=6 Hz).

EXAMPLE 3

Starting from tert-butyl 3-dodecanoyloxytetradecanoate (165 mg) prepared by the method described in Preparation 3-(2) and N-glycyl-L-serine (162 mg), N-[N-(3-dodecanoyloxytetradecanoyl)glycyl]-L-serine (120 mg) was obtained as an amorphous powder according to similar manner to that of Example 1.

IR (CHCl$_3$): 3300, 2920, 2850, 1715, 1645 cm$^{-1}$.

NMR (CDCl$_3$: CD$_3$OD=1:1, δ): 5.24 (1H, m), 4.6 (1H, m), 3.66 to 4.02 (4H, m), 2.54 (2H, d, J=6 Hz), 2.3 (2H, t, J=7 Hz), 1.0 to 1.9 (38H, m), 0.88 (6H, t, J=6 Hz).

EXAMPLE 4

Starting from tert-butyl 3-hexadecanoyloxyoctanoate (130 mg) prepared by the method described in Preparation 4-(2) and N-glycyl-L-serine (139 mg), N-[N-(3-hexadecanoyloxyoctanoyl)glycyl]-L-serine (103 mg) was obtained as an amorphous powder according to similar manner to that of Example 1.

IR (Nujol): 3350, 2910, 2850, 1720, 1650 cm$^{-1}$.

NMR (CDCl$_3$: CD$_3$OD=1:1, δ): 5.3 (1H, m), 4.35 (1H, m), 3.65 to 4.1 (4H, m), 2.58 (2H, d, J=6 Hz), 2.34 (2H, t, J=6 Hz), 1.0 to 1.9 (34H, m), 0.9 (6H, t, J=6 Hz).

EXAMPLE 5

Starting from tert-butyl 3-hexanoyloxyoctanoate (157 mg) prepared by the method described in Preparation 5 and N-glycyl-L-serine (243 mg), N-[N-(3-hexanoyloxyoctanoyl)glycyl]-L-serine (105 mg) was obtained as an oil according to similar manner to that of Example 1.

IR (CHCl$_3$): 3300, 2940, 2860, 1715, 1650 cm$^{-1}$.

NMR (CDCl$_3$: CD$_3$OD=1:1, δ): 5.2 (1H, m), 4.3 (1H, m), 3.5 to 4.0 (4H, m), 2.55 (2H, d, J=6 Hz), 2.28 (2H, t, J=6 Hz), 1.8 to 1.0 (14H, m), 0.88 (6H, t, J=6 Hz).

EXAMPLE 6

3-Butanoyloxyhexanoic acid (234 mg) prepared by the method described in Preparation 6-(2) and N-hydroxysuccinimide (133 mg) was dissolved in dioxane (3 ml). N,N'-Dicyclohexylcarbodiimide (239 mg) was added thereto under ice cooling. The mixture was reached to room temperature and stirred at ambient temperature over night. The crystallized N,N'-dicyclohexyl urea was filtered off and the filtrate was concentrated to give a residue which was dissolved in N,N-dimethylformamide (5 ml). To this solution was added a solution of N-glycyl-L-serine (324 mg) and triethylamine (280 μl) in water (3 ml) at 0° C. The resulting mixture was reached to room temperature and stirred at ambient temperature overnight. The reaction mixture was acidified with 1 N hydrochloric acid, extracted with ethyl acetate, washed with water and dried over magnesium sulfate. Ethyl acetate was distilled off to give a residue which was subjected to preparative thin layer chromatography (Merck, 0.25 mm×5) and eluted with a mixture of benzene, dioxane and acetic acid (10:5:1). The band containing the object compound was extracted with a mixture of methanol and chloroform (3:7) and the solvent was evaporated off under reduced pressure to afford a wax of N-[N-(3-butanoyloxyhexanoyl)glycyl]-L-serine.

IR (CHCl$_3$): 3350, 2950, 1715, 1650 cm$^{-1}$.

NMR (CDCl$_3$-CD$_3$OD=1:1, δ): 5.25 (1H, m), 4.6 (1H, m), 3.9 (4H, m), 2.52 (2H, d, J=6 Hz), 2.3 (2H, t, J=7 Hz), 1.8 to 1.2 (6H, m), 0.95 (6H, t, J=7 Hz).

EXAMPLE 7

3-Hexadecanoyloxyoctadecanoic acid (150 mg) prepared by the method described in Preparation 2-(3) and N-hydroxysuccinimide (38 mg) were dissolved in dioxane (3 ml). N,N-Dicyclohexylcarbodiimide (68 mg) was added thereto under ice cooling. The mixture was reached to room temperature and stirred at ambient temperature overnight. The crystallized urea was filtered off and the filtrate was concentrated to give a residue which was dissolved in N,N-dimethylformamide (7 ml). To this solution was added a solution of N-β-alanyl-L-threonine (110 mg) and triethylamine (100 μl) in water (5 ml) at 0° C. The resulting mixture was reached to room temperature and stirred at ambient temperature overnight. The reaction mixture was acidified with 1 N hydrochloric acid, extracted with ethyl acetate, washed with water and dried over magnesium sulfate. Ethyl acetate was distilled off to give a residue which was subjected to preparative thin layer chromatography (Merck, 0.25 mm×5) and eluted with a mixture of benzene, dioxane and acetic acid (10:5:1). The band containing the object compound was extracted with a mixture of methanol and chloroform (3:7) and the solvent was evaporated off under reduced pressure to afford powder of N-[N-(3-hexadecanoyloxyoctadecanoyl)-β-alanyl]-L-threonine (95 mg).

IR (CHCl$_3$): 3350, 2925, 2850, 1725, 1640 cm$^{-1}$.

NMR (CDCl$_3$: CD$_3$OD=1:1, δ): 5.2 (1H, m), 4.5 to 4.1 (2H, m), 3.42 (2H, m), 2.6 to 2.2 (6H, m), 1.8 to 1.0 (57H, m), 0.9 (6H, t, J=6 Hz).

EXAMPLE 8

15-Methyl-3-(13-methyltetradecanoyloxy)hexadecanoic acid (140 mg) prepared by the method described in Preparation 1-(3) and N-hydroxysuccinimide (34 mg) were dissolved in dioxane (2.5 ml). N,N-Dicyclohexylcarbodiimide (63 mg) was added thereto under ice cooling. The mixture was reached to room temperature and stirred at ambient temperature overnight. The crystallized urea was filtered off and the filtrate was concentrated to give a residue which was dissolved in N,N-dimethylformamide (5 ml). To this solution was added a solution of β-alanyl-L-threonine (100 mg) and triethylamine (90 μl) in water (3 ml) at 0° C. The resulting mixture was reached to room temperature and stirred at ambient temperature overnight. The reaction mixture was acidified with 1 N hydrochloric acid, extracted with ethyl acetate, washed with water and dried over magnesium sulfate. Ethyl acetate was distilled off to give a residue which was subjected to preparative thin layer chromatography (Merck, 0.25 mm×5) and eluted with a mixture of benzene, dioxane and acetic acid (10:5:1). The band containing the object compound was extracted with methanol and chloroform (3:7) and the solvent was evaporated off under reduced pressure to afford a wax of N-[N-[15-methyl-3-(13-methyltetradecanoyloxy)hexadecanoyl]-β-alanyl]-L-threonine (100 mg).

IR (CHCl$_3$): 3300, 2920, 2850, 1715, 1650 cm$^{-1}$.

NMR (CDCl$_3$-CD$_3$OD, δ): 5.2 (1H, m), 4.6 to 4.2 (2H, m), 3.44 (2H, m), 2.6 to 2.2 (6H, m), 1.8 to 1.0 (47H, m), 0.85 (12H, d, J=6 Hz).

EXAMPLE 9

15-Methyl-3-(13-methyltetradecanoyloxy)hexadecanoic acid (102 mg) prepared by the method described in Preparation 1-(3) and N-hydroxysuccinimide (25 mg) were dissolved in dioxane (2 ml). N,N-Dicyclohexylcarbodiimide (46 mg) was added thereto under ice-cooling. The mixture was reached to room temperature and stirred at ambient temperature overnight. The crystallized urea was filtered off and the filtrate was concentrated to give a residue which was dissolved in N,N-dimethylformamide (3 ml). To this solution was added a solution of N-β-alanyl-L-serine (100 mg) and triethylamine (100 μl) in water (2 ml) at 0° C. The resulting mixture was reached to room temperature and stirred at ambient temperature overnight. The reaction mixture was acidified with 1 N hydrochloric acid, extracted with ethyl acetate, washed with water and dried over magnesium sulfate. Ethyl acetate was distilled off to give a residue (128 mg) which was subjected to preparative thin layer chromatography (Merck, 0.25 mm×5) and eluted with a mixture of benzene, dioxane and acetic acid (10:5:1). The band containing the object compound was extracted with a mixture of methanol and chloroform (3:7) and the solvent was evaporated off under reduced pressure to afford a wax of N-[N-[15-methyl-3-(13-methyltetradecanoyloxy)hexadecanoyl]-β-alanyl]-L-serine (69 mg).

IR (Nujol): 3350, 2920, 2850, 1720, 1640 cm$^{-1}$.

NMR (CDCl$_3$-CD$_3$OD=1:1, δ): 5.24 (1H, m), 4.6 (1H, m), 3.94 (2H, m), 3.5 (2H, m), 2.5 to 2.27 (6H, m), 1.8 to 1.0 (44H, m), 0.85 (12H, d, J=6 Hz).

EXAMPLE 10

3-Hexadecanoyloxyoctadecanoic acid (150 mg) prepared by the method described in Preparation 2-(3) and N-hydroxysuccinimide (38 mg) were dissolved in dioxane (2 ml). N,N-Dicyclohexylcarbodiimide (68 mg) was added thereto under ice cooling. The mixture was reached to ambient temperature and stirred at the same temperature overnight. The crystallized urea was filtered off and the filtrate was concentrated to give a residue which was dissolved in N,N-dimethylformamide (7 ml). To this solution was added a solution of N-β-alanyl-L-serine (100 mg) and triethylamine (100 μl) in water (4 ml) at 0° C. The resulting mixture was reached to ambient temperature and stirred at the same temperature overnight. The reaction mixture was acidified with 1 N hydrochloric acid, extracted with ethyl acetate, washed with water and dried over magnesium sulfate. Ethyl acetate was distilled off to give a residue which was subjected to preparative thin layer chromatography (Merck, 0.25 mm×5) and eluted with a mixture of benzene, dioxane and acetic acid (10:5:1). The band containing the object compound was extracted with a mixture of methanol and chloroform (3:7) and the solvent was evaporated off under reduced pressure to afford powder of N-[N-(3-hexadecanoyloxyoctadecanoyl)-β-alanyl]-L-serine (78 mg).

IR (CHCl$_3$): 3300, 2925, 2850, 1720, 1650 cm$^{-1}$.

NMR (CD$_3$Cl-CD$_3$OD=1:1, δ): 5.2 (1H, m), 4.4 (1H, m), 4.6 to 4.2 (2H, m), 3.44 (2H, m), 2.6 to 2.1 (6H, m), 2.1 to 1.1 (54H, m), 0.9 (6H, t, J=6 Hz).

EXAMPLE 11

Starting from 15-methyl-3-(13-methyltetradecanoyloxy)hexadecanoic acid (102 mg) prepared by the method described in Preparation 1-(3) and N-glycyl-L-threonine (72 mg), N-[N-[15-methyl-3-(13-methyltetradecanoyloxy)hexadecanoyl]glycyl]-L-threonine (66 mg) was obtained as a wax according to similar manner to that of Example 6.

IR (Nujol): 3300, 2950, 2850, 1720, 1650 cm$^{-1}$.

NMR (CDCl$_3$: CH$_3$OD=1:1, δ): 5.20 (1H, m), 4.5 (1H, m), 4.3 (1H, m), 3.93 (2H, broad s), 2.55 (2H, d, J=6 Hz), 2.34 (2H, t, J=7 Hz), 1.0 to 2.0 (47H, m), 0.85 (12H, d, J=6 Hz).

EXAMPLE 12

15-Methyl-3-(13-methyltetradecanoyloxy)hexadecanoic acid (80 mg) prepared by the method described in Preparation 1-(3) and N-hydroxysuccinimide (20 mg) were dissolved in dioxane (2 ml). N,N-Dicyclohexylcarbodiimide (37 mg) was added thereto under ice cooling. The mixture was reached to ambient temperature and stirred at the same temperature overnight. The crystallized urea was filtered off and the filtrate was concentrated to give a residue which was dissolved in N,N-dimethylformamide (3 ml). To the solution was added a solution of N-L-alanyl-L-serine trifluoroacetate (94 mg) and triethylamine (90 μl) in water (2 ml) at 0° C. The resulting mixture was reached to ambient temperature and stirred at the same temperature overnight. The reaction mixture was acidified with 1 N hydrochloric acid, extracted with ethyl acetate, washed with water and dried over magnesium sulfate. Ethyl acetate was distilled off to give a residue which was subjected to preparative thin layer chromatography (Merck, 0.25 mm×5) and eluted with a mixture of benzene, dioxane and acetic acid (10:5:1). The band containing the object compound was extracted with a mixture of methanol and chloroform (3:7) and the solvent was evaporated off under reduced pressure to afford a wax of N-[N-[15-methyl-3-(13-methyltetradecanoyloxy)hexadecanoyl]L-alanyl]-L-serine (60 mg).

IR (CHCl$_3$): 3300, 2920, 2850, 1720, 1650 cm$^{-1}$.

NMR (CDCl$_3$: CD$_3$OD=1:1, δ): 5.2 (1H, m), 4.6 to 4.3 (2H, m), 3.87 (2H, m), 2.44 (2H, d, J=6 Hz), 2.3 (2H, t, J=7 Hz), 1.8 to 1.0 (47H, m), 0.85 (12H, d, J=6 Hz).

EXAMPLE 13

Starting from 15-methyl-3-(13-methyltetradecanoyloxy)hexadecanoic acid (140 mg) prepared by the method described in Preparation 1-(3) and L-alanyl-L-threonine trifluoroacetate (303 mg), N-[N-[15-methyl-3-(13-methyltetradecanoyloxy)hexadecanoyl]-L-alanyl]-L-threonine (110 mg) was obtained as a wax according to similar manner to that of Example 12.

IR (CHCl$_3$): 3400, 2940, 2860, 1720, 1650 cm$^{-1}$.

NMR (CDCl$_3$-CD$_3$OD=1:1, δ): 5.2 (1H, m), 4.6 to 4.3 (2H, m), 2.6 to 2.05 (5H, m), 1.8 to 1.0 (50H, m), 0.85 (12H, d, J=6 Hz).

EXAMPLE 14

Starting from 3-hexadecanoyloxyoctadecanoic acid (150 mg) prepared by the method described in Preparation 2(3) and N-L-alanyl-L-threonine (303 mg), N-[N-(3-hexadecanoyloxyoctadecanoyl)-L-alanyl]-L-threonine (164 mg) was obtained as powder according to similar manner to that of Example 12.

IR (CHCl$_3$): 3400, 2925, 2850, 1720, 1650, 1600 cm$^{-1}$.

NMR (CDCl$_3$: CD$_3$OD=1:1, δ): 5.2 (1H, m), 4.5 to 4.2 (3H, m), 2.6 to 2.1 (4H, m), 1.8 to 1.0 (60H, m), 0.9 (6H, t, J=6 Hz).

EXAMPLE 15

Starting from 15-methyl-3-(13-methyltetradecanoyloxy)hexadecanoic acid (102 mg) prepared by the method described in Preparation 1-(3) and N-glycyl-L-phenylalanine (62 mg) N-[N-[15-methyl-3-(13-methyltetradecanoyloxy)hexadecanoyl]glycyl]-L-phenylalanine was obtained as a wax according to similar manner to that of Example 6.

IR (CHCl$_3$): 3350, 2920, 2850, 1720, 1650 cm$^{-1}$.

NMR (CDCl$_3$: CD$_3$OD=1:1, δ): 7.2 (5H, broad s), 5.2 (1H, m), 4.55 (1H, m), 3.8 (2H, m), 3.1 (2H, m), 2.45 (2H, d, J=6 Hz), 2.26 (2H, t, J=7 Hz), 1.8 to 1.0 (44H, m), 0.85 (12H, d, J=6 Hz).

EXAMPLE 16

Starting from 15-methyl-3-(13-methyltetradecanoyloxy)hexadecanoic acid (102 mg) prepared by the method described in Preparation 1-(3) and N-β-alanyl-L-histidine (100 mg), N-[N-[15-methyl-3-(13-methyltetradecanoyloxy)hexadecanoyl]-β-alanyl]-L-histidine (41 mg) was obtained as a wax according to similar manner to that of Example 6.

IR (CDCl$_3$): 3400, 2920, 2850, 1710, 1650 cm$^{-1}$.

NMR (CDCl$_3$: CD$_3$OD=1:1,δ): 7.1 (1H, m), 5.2 (1H, m), 4.55 (1H, m), 3.35 (2H, m), 2.7 (2H, broad s), 2.7 to 2.2 (6H, m), 1.8 to 1.0 (44H, m), 0.85 (12H, d, J=6 Hz).

EXAMPLE 17

Starting from 15-methyl-3-(13-methyltetradecanoyloxy)hexadecanoic acid (102 mg) prepared by the method described in Preparation 1-(3) and N-glycyl-L-O-benzyltyrosine trifluoroacetate (300 mg), N-[N-[15-methyl-3-(13-methyltetradecanoyloxy)hexadecanoyl]-glycyl]-L-O-benzyltyrosine (68 mg) was obtained as a wax according to similar manner to that of Example 12.

IR (Nujol): 3260, 2900, 2850, 1720, 1635, 720, 685 cm$^{-1}$.

EXAMPLE 18

N-[N-[15-Methyl-3-(13-methyltetradecanoyloxy)hexadecanoyl]glycyl]-L-O-benzyltyrosine (60 mg) prepared in Example 17 was dissolved in methanol (8 ml) and ethyl acetate (2 ml) and a mixture of palladium black (50 mg) and water (2 ml) was added thereto. The mixture was subjected to catalytic hydrogenation. The reaction mixture was filtered and the filtrate was condensed. The residue was dried up by using high vacuum pump to afford a wax of N-[N-[15-methyl-3-(13-methyltetradecanoyloxy)hexadecanoyl]glycyl]-L-tyrosine (51 mg).

IR (Nujol): 3350, 2950, 2850, 1720, 1650 cm$^{-1}$.

NMR (CDCl$_3$: CD$_3$OD=1:1, δ): 7.2 (2H, d, J=8 Hz), 6.6 (2H, d, J=8 Hz), 5.2 (1H, m), 4.6 to 4.2 (3H, m), 3.05 (2H, m), 2.45 (2H, d, J=6 Hz), 2.32 (2H, t, J=7 Hz), 1.8 to 1.0 (44H, m), 0.85 (12H, d, J=6 Hz).

EXAMPLE 19

Starting from 15-methyl-3-(13-methyltetradecanoyloxy)hexadecanoic acid (102 mg) prepared by the method described in Preparation 1-(3) and glycine (75 mg), N-[15-methyl-3-(13-methyltetradecanoyloxy)hexadecanoyl]glycine (57 mg) was obtained as a wax according to similar manner to that of Example 6.

IR (CHCl$_3$): 3400, 2925, 2850, 1720, 1660 cm$^{-1}$.

NMR (CDCl$_3$-CD$_3$OD=1:1, δ): 5.22 (1H, m), 3.9 (2H, s), 2.54 (2H, d, J=6 Hz), 2.32 (2H, t, J=6 Hz), 1.8 to 1.0 (44H, m), 0.85 (12H, d, J=6 Hz).

EXAMPLE 20

Starting from 15-methyl-3-(13-methyltetradecanoyloxy)hexadecanoic acid (102 mg) prepared by the method described in Preparation 1-(3) and L-serine (105 mg), N-[15-methyl-3-(13-methyltetradecanoyloxy)hexadecanoyl]-L-serine (59 mg) was obtained as a wax according to similar manner to that of Example 6.

IR (CHCl$_3$): 3400, 2940, 2850, 1720, 1650 cm$^{-1}$.

NMR (CDCl$_3$-CD$_3$OD=1:1, δ): 5.24 (1H, m), 4.6 (1H, m), 3.85 (2H, m), 2.52 (2H, d, J=6 Hz), 2.32 (2H, t, J=7 Hz), 1.8 to 1.0 (44H, m), 0.85 (12H, d, J=6 Hz).

EXAMPLE 21

A culture medium (100 ml, pH 7.0) containing 0.7% meat extract, 1% of peptone and 0.3% of sodium chloride was poured into each of 16 Erlenmeyer-flasks and sterilized at 120° C. for 20 minutes. A loopful of slant culture of Flavobacterium sp. No. 3559 ATCC 31701 was inoculated into each of the medium and cultured at 30° C. for 48 hours. The resultant culture was inoculated into a medium (160 l) containing a medium mentioned above in a 200 liter tank which had been sterilized at 120° C. for 20 minutes and cultured at 30° C. for 72 hours. The culture broth thus obtained was filtered to get cultured cells (2 kg).

The cultured cells were extracted with 10 liters of acetone and the extract was concentrated in vacuo to a volume of 1 liter. After adjusting to pH 2.0, the concentrate was extracted with 1 liter of ethyl acetate. The extract was concentrated in vacuo and the concentrate was subjected to a column chromatography of silicic acid (SILICAR CC-4, made by Mallinckrodt). The column was washed with hexane (1 liter) and hexane-ethyl acetate(3:1) (2 liters), and then eluted with ethyl acetate (2 liters). The eluate was dried up in vacuo.

The resultant residue was subjected to a reverse phase column chromatography packed with NS-gel (made by NIPPON-SEIMITSU-KAGAKU) (1 liter), and then washed and eluted with methanol. The fractions containing the object compounds were collected and concentrated to give a waxy mixture of the compound (I'-A), compound (I'-B), compound (I'-C) and compound (I'-D).

The waxy mixture was subjected to a high pressure liquid chromatography in the following conditions.

Apparatus: An apparatus for liquid chromatography M-6000 A type (made by WATERS ASSOCIATES, INC.)
Stationary phase: Bondapack C18 (made by WATERS ASSOCIATES, INC.)
Length of column: 61 cm
Internal diameter of column: 7 mm
Mobile phase: methanol-water (95:5) containing 0.01% of acetic acid
Column temperature: Ambient
Flow rate: 9.9 ml/minutes
Detector: Refractive index (Model R401 made by WATERS ASSOCIATES INC.)

The liquid chromatogram gave the fraction A (retention time: 21.0 minutes) which contains the compound (I'-A) and compound (I'-B) and the fraction B (retention time: 28.0 minutes) which contains the compound (I'-C) and compound (I'-D).

These fractions A and B were further subjected to a high pressure liquid chromatography, respectively.

(1) Separation of the compound (I'-A) and compound (I'-B):
Apparatus was the same to the above.
Stationary phase: μBondapack $C_{18}$ (made by WATERS ASSOCIATES INC.)
Length of column: 30 cm
Internal diameter of column: 4 mm
Mobile phase: methanol-water (90:10) containing 0.01% of acetic acid
Column temperature: ambient
Flow rate: 2 ml/minutes The liquid chromatogram gave the compound (I'-A) (10 mg) (retention time: 10.8 minutes) and the compound (I'-B) (110 mg) (retention time: 12.2 minutes), respectively.

(2) Separation of the compound (I'-C) and compound (I'-D).

The compound (I'-C) (15 mg) (retention time: 13.2 minutes) and the compound (I'-D) (150 mg) (retention time: 15.3 minutes) were obtained in a similar method to the above, respectively.

EXAMPLE 22

To a solution of a compound (I'-D) (17 mg) in methanol (3 ml) was added excess diazomethane in ether. The resulting solution was allowed to stand for 5 hours at room temperature, and then the solvent was evaporated off. The residue was purified by preparative thin layer chromatography and eluted with a mixture of chloroform and methanol (9:1). The band containing the object compound was extracted with a mixture of methanol and chloroform (1:5), and the solvent was evaporated off under reduced pressure to afford a powder of a methyl ester of a compound (I'-D) (14 mg).

IR(CHCl$_3$): 3400, 2940, 2850, 1730, 1660 cm$^{-1}$.
NMR (CDCl$_3$, δ): 7.26(1H, m), 6.7(1H, m), 5.25(1H, m), 4.6(1H, m), 3.96(4H, m), 3.77(3H, s), 2.5(2H, d, J=7 Hz), 2.3(2H, t, J=7 Hz), 1.0 to 1.8(44H, m), 0.85(12H, d, J=6 Hz).

EXAMPLE 23

Starting from a compound (I'-A) (10 mg) prepared by the method described in Example 21 a methyl ester of a compound (I'-A) (8 mg) was obtained as a powder according to similar manner to that of Example 22.

IR(CHCl$_3$): 3400, 2920, 2850, 1725, 1660 cm$^{-1}$.
NMR(CDCl$_3$, δ): 7.15(1H, m), 6.6(1H, m), 5.4 to 5.1(3H, m), 4.6(1H, m), 3.96(4H, m), 3.77(3H, s), 2.5(2H, d, J=6 Hz), 2.35(4H, m), 2.0(2H, m), 1.8 to 1.0(34H, m), 0.85(12H, d, J=6 Hz).

EXAMPLE 24

Starting from a compound (I'-B) (15 mg) prepared by the method described in Example 21 a methyl ester of a compound (I'-B) (10 mg) was obtained as a powder according to similar manner to that of Example 22.

IR(CHCl$_3$): 3400, 2920, 2850, 1725, 1660 cm$^{-1}$.
NMR(CDCl$_3$, δ): 7.15(1H, m), 6.6(1H, m), 5.4 to 5.1(3H, m), 4.6(1H, m), 3.96(4H, m), 3.77 (3H, s), 2.5(2H, d, J=6 Hz), 2.35(4H, m), 2.0(2H, m), 1.8 to 1.0(36H, m), 0.85(12H, d, J=6 Hz).

EXAMPLE 25

Starting from a compound (I'-C) (13 mg) prepared by the method described in Example 21 a methyl ester of a compound (I'-C) (10 mg) was obtained as a powder according to similar manner to that of Example 22.

IR(CHCl$_3$): 3400, 2920, 2840, 1725, 1660 cm$^{-1}$.
NMR(CDCl$_3$, δ): 7.25(1H, m), 6.7(1H, m), 5.15(1H, m), 4.6(1H, m), 3.97(4H, m), 3.78(3H, s), 2.5(2H, d, J=6 Hz), 2.3(2H, t, J=7 Hz), 1.8 to 1.0(42H, m), 0.85(12H, d, J=6 Hz).

EXAMPLE 26

Starting from 3-hexadecanoyloxyoctadecanoic acid (1 g) prepared by the method described in Preparation 2 and L-phenylalanine (1 g), N-(3-hexadecanoyloxyoctadecanoyl)-L-phenylalanine (500 mg) was obtained as powders according to a similar manner to that of Example 6.

NMR (CDCl$_3$-CD$_3$OD, δ): 5.2 (1H, m), 4.6 (1H, m), 3.2 (2H, m), 2.2 (4H, m), 1.8 to 1.1 (60H, m), 0.86 (6H, t, J=6 Hz).

EXAMPLE 27

Starting from 3-hexadecanoyloxyoctadecanoic acid (400 mg) prepared by the method described in Preparation 2 and glycine (300 mg), N-(3-hexadecanoyloxyoctadecanoyl)glycine (260 mg) was obtained as powders according to a similar manner to that of Example 6.

NMR (CDCl$_3$-CD$_3$OD, δ): 3.95 (2H, s), 2.5 (2H, d, J=7 Hz), 2.2 (2H, t, J=7 Hz), 1.9 to 1.1 (60H, m), 0.95 (6H, t, J=7 Hz).

EXAMPLE 28

Starting from 3-hexadecanoyloxyoctadecanoic acid (10.8 g) prepared by the method described in Preparation 2 and L-valine (5.85 g), N-(3-hexadecanoyloxyoctadecanoyl)-L-valine (8 g) was obtained as crystals according to a similar manner to that of Example 6.

IR (CHCl$_3$): 2930, 2850, 1720, 1660 cm$^{-1}$.

NMR (CDCl$_3$, δ): 5.2 (1H, m), 4.5 (1H, m), 2.5 (2H, d, J=6 Hz), 2.35 (2H, t, J=6 Hz), 1.8 to 1.1 (61H, m), 0.95 (6H, t, J=7 Hz).

EXAMPLE 29

To a solution of N-(3-hexadecanoyloxyoctadecanoyl)-L-valine (1.27 g) prepared by the method of Example 28 in dioxane (15 ml) were added N-hydroxysuccinimide (230 mg) and N,N'-dicyclohexylcarbodiimide (440 mg). The mixture was stirred-overnight at room temperature. The crystallized N,N'-dicyclohexylurea was removed by filtration, and the filtrate was condensed under reduced pressure.

The residue was dissolved in tetrahydrofuran (100 ml), and to this solution were added a solution of L-threonine (950 mg) in water (50 ml) and triethylamine (1.1 ml). The resulting mixture was stirred at ambient temperature for 5 hours. The reaction mixture was acidified with 1 N hydrochloric acid solution, extracted with ethyl acetate, washed with water, and dried over magnesium sulfate. Ethyl acetate was distilled off to give a residue, which was purified by column chromatography on silica gel. Elution with a mixture of chloroform and methyl alcohol (10:1) afforded powders of N-[N-(3-hexadecanoyloxyoctadecanoyl)-L-valyl]-L-threonine (500 mg).

IR (CHCl$_3$): 3400, 2920, 2850, 1720, 1650 cm$^{-1}$.

NMR (CDCl$_3$-CD$_3$OD, δ): 5.2 (1H, m), 4.4 (3H, m), 2.5 to 2.1 (4H, m), 1.8 to 1.1 (58H, m), 0.9 (12H, m).

EXAMPLE 30

Starting from N-(3-hexadecanoyloxyoctadecanoyl)-L-valine (1 g) prepared by the method of Example 28 and L-phenylalanine (777 mg), N-[N-(3-hexadecanoyloxyoctadecanoyl)-L-valyl]-L-phenylalanine (900 mg) was obtained as powders according to a similar manner to that of Example 29.

IR (CHCl$_3$): 3450, 2940, 2860, 1720, 1650 cm$^{-1}$.

NMR (CDCl$_3$-CD$_3$OD, δ): 7.2 (5H, m), 5.2 (1H, m), 4.8 (1H, m), 4.2 (1H, m), 3.1 (2H, m), 2.5 to 2.1 (4H, m), 1.9 to 1.1 (55H, m), 0.9 (12H, m).

EXAMPLE 31

Starting from 3-hexadecanoyloxyoctadecanoic acid (10.8 g) prepared by the method described in Preparation 2 and β-alanine (5.36 g), N-(3-hexadecanoyloxyoctadecanoyl)-β-alanine (9.33 g) was obtained as crystals according to a similar manner to that of Example 6.

IR (CHCl$_3$): 2940, 2850, 1720, 1660 cm$^{-1}$

NMR (CDCl$_3$-CD$_3$OD, δ): 5.2 (1H, m), 3.5 (2H, m), 2.7 to 2.3 (6H, m), 1.9 to 1.2 (54H, m), 0.95 (6H, t, J=7 Hz).

EXAMPLE 32

Starting from N-(3-hexadecanoyloxyoctadecanoyl)-β-alanine (1.52 g) prepared by the method of Example 31 and L-phenylalanine (1.65 g), N-[N-(3-hexadecanoyloxyoctadecanoyl)-β-alanyl]-L-phenylalanine (1.64 g) was obtained as crystals according to a similar manner to that of Example 29.

IR (CHCl$_3$): 3450, 2940, 2850, 1720, 1660 cm$^{-1}$.

NMR (CDCl$_3$-CD$_3$OD, δ): 7.2 (5H, m), 5.2 (1H, m), 4.8 (1H, m), 3.2 to 3.4 (4H, m), 2.4 to 2.2 (6H, m), 1.9 to 1.1 (54H, m), 0.95 (6H, t, J=6 Hz).

EXAMPLE 33

Starting from 3-hexadecanoyloxyoctadecanoic acid (5.38 g) prepared by the method described in Preparation 2 and 5-aminovaleric acid (5.0 g), 5-(3-hexadecanoyloxyoctadecanoyl)aminovaleric acid (5.7 g) was obtained as cristals according to a similar manner to that of Example 6. M.p. 66°-7°.

IR (CHCl$_3$): 2940, 2860, 1720, 1660 cm$^{-1}$.

NMR (CDCl$_3$-CD$_3$OD, δ): 5.2 (1H, m), 3.25 (2H, m), 2.4 (6H, m), 1.9 to 1.1 (58H, m), 0.95 (6H, t, J=6 Hz).

EXAMPLE 34

Starting from 5-(3-hexadecanoyloxyoctadecanoyl)aminovaleric acid (1.27 g) and L-threonine (950 mg), N-[5-(3-hexadecanoyloxyoctadecanoyl)aminovaleryl]-L-threonine (1.3 g) was obtained as crystals according to a similar manner to that of Example 6.

IR (CHCl$_3$): 3450, 3350, 2940, 2860, 1720, 1660 cm$^{-1}$.

NMR (CDCl$_3$-CD$_3$OD, δ): 5.2 (1H, m), 4.5 (1H, m), 4.2 (1H, m), 3.25 (2H, m), 2.4 (6H, m), 1.9 to 1.1 (61H, m), 0.95 (6H, t, J=6 Hz).

EXAMPLE 35

Starting from 2-hexadecanoyloxyhexadecanoic acid (128 mg) prepared by the method described in Preparation 7 and N-glycyl-L-serine (162 mg), N-[N-(2-hexadecanoyloxyhexadecanoyl)glycyl]-L-serine (100 mg) was obtained as powders according to a similar manner to that of Example 6.

NMR (CDCl$_3$-CD$_3$OD, δ): 5.0 (1H, m), 3.9 (4H, m), 2.4 (2H, m), 2.0 to 1.0 (52H, m), 0.85 (6H, t, J=6 Hz).

EXAMPLE 36

Starting from 2-hexadecanoyloxyhexadecanoic acid (200 mg) prepared by the method described in Preparation 7 and N-β-alanyl-L-threonine (190 mg), N-[N-(2-hexadecanoyloxyhexadecanoyl)-β-alanyl]-L-threonine (230 mg) was obtained as crystals according to a similar manner to that of Example 6.

IR (CHCl$_3$): 3350, 2940, 2860, 1730, 1660 cm$^{-1}$.

NMR (CDCl$_3$-CD$_3$OD, δ): 5.0 (1H, t, J=5 Hz), 4.6 to 4.3 (2H, m), 3.5 (2H, m), 2.5 (4H, m), 2.0 to 1.1 (55H, m), 0.9 (6H, t, J=6 Hz).

EXAMPLE 37

Starting from 2-hexadecanoyloxyhexadecanoic acid (2.55 g) prepared by the method described in Preparation 7 and L-valine (2.34 g), N-(2-hexadecanoyloxyhexadecanoyl)-L-valine (2.5 g) was obtained as crystals according to a similar manner to that of Example 6.

IR (CHCl$_3$): 2940, 2860, 1728, 1680 cm$^{-1}$.

NMR (CDCl$_3$-CD$_3$OD, δ): 5.15 (1H, m), 4.5 (1H, m), 2.4 (2H, m), 2.0 to 1.1 (53H, m), 0.9 (12H, m).

EXAMPLE 38

Starting from N-(3-hexadecanoyloxyoctadecanoyl)glycine (2.6 g) prepared by the method described in Example 27 and L-phenylalanine (1.65 g), N-[N-(3-hexadecanoyloxyoctadecanoyl)glycyl]-L-phenylalanine (2.1 g) was obtained as powders according to a similar manner to that of Example 29.

IR (Nujol): 3300, 2925, 2850, 1720, 1650 cm$^{-1}$.

NMR (CDCl₃-CD₃OD, δ): 7.3 (5H, s), 5.2 (1H, m), 4.5 (1H, t), 3.95 (2H, s), 3.1 (2H, d), 2.6 to 2.1 (4H, m), 2.1 to 1.1 (54H, m), 0.9 (6H, t, J=6 Hz).

EXAMPLE 39

Starting from 3-(9-octadecenoyloxy)-11-eicosenoic acid (3.2 g) prepared by the method described in Preparation 8 and L-valine (4.42 g), N-[3-(9-octadecenoyloxy)-11-eicosenoyl]-L-valine (2.7 g) was obtained as powders according to a similar manner to that of Example 6.

EXAMPLE 40

Starting from 3-(9-octadecenoyloxy)-11-eicosenoic acid (2.6 g) prepared by the method described in Preparation 8 and glycine (1.2 g), N-[3-(9-octadecenoyloxy)-11-eicosenoyl]glycine (2 g) was obtained as powders in a similar manner to that of Example 6.

EXAMPLE 42

Starting from N-[3-(9-octadecenoyloxy)-11-eicosenoyl]glycine (2.0 g) prepared by the method described in Example 40 and L-phenylalanine (2.64 g), N-[N-[3-(9-octadecenoyloxy)-11-eicosenoyl]glycyl]-L-phenylalanine (1.8 g) was obtained as powders according to a similar manner to that of Example 29.

IR (Nujol): 3300, 2925, 2850, 1720, 1650 cm⁻¹.

NMR (CDCl₃-CD₃OD, δ): 5.3 (4H, t), 5.2 (1H, m), 4.5 (1H, t), 3.95 (2H, s), 2.6 to 2.1 (4H, m), 2.1 to 1.8 (8H, m), 1.7 to 1.0 (46H, m), 0.9 (6H, t, J=6 Hz), 3.1 (2H, d), 7.3 (5H, s).

EXAMPLE 42

Starting from 3-(9-octadecenoyloxy)-11-eicosenoic acid (0.54 g) and N-glycyl-L-serine (0.4 g), N-[N-[3-(9-octadecenoyloxy)-11-eicosenoyl]glycyl]-L-serine (0.42 g) was obtained as powders according to a similar manner to that of Example 6.

IR (Nujol): 3300, 2925, 2850, 1720, 1650 cm⁻¹.

NMR (CDCl₃-CD₃OD, δ): 5.3 (4H, t), 5.2 (1H, m), 4.57 (1H, t), 3.8 to 4.0 (4H, m), 2.6 to 2.1 (4H, m), 2.1 to 1.8 (8H, m), 1.7 to 1.0 (46H, m), 0.9 (6H, t, J=6 Hz).

EXAMPLE 43

N-(3-hexadecanoyloxyoctadecanoyl)glycine (1.3 g) prepared by the method described in Example 27 and L-tryptophan (1.45 g), N-[N-(3-hexadecanoyloxyoctadecanoyl)glycyl]-L-tryptophan (820 mg) was obtained as powders according to a similar manner to that of Example 29.

IR (CHCl₃): 3350, 2950, 2880, 1720, 1650 cm⁻¹.

NMR (CDCl₃-CD₃OD, δ): 7.7 to 6.8 (5H, m), 5.2 (1H, m), 4.65 (1H, m), 3.7 (2H, m), 3.5 (2H, m), 2.5 to 1.9 (4H, m), 1.8 to 1.1 (54H, m), 0.9 (6H, t, J=6 Hz).

What we claim is:

1. A compound of the formula:

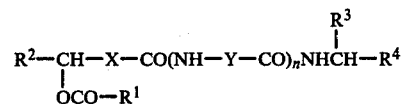

wherein

R¹ and R² are each alkyl or alkenyl;

R³ is hydrogen, lower alkyl, hydroxy(lower)alkyl, heterocyclic(lower)alkyl or ar(lower)alkyl, wherein the aryl moiety may have hydroxy or protected hydroxy;

R⁴ is carboxy, esterified carboxy, carboxy(lower)alkyl or esterified carboxy(lower)alkyl;

X is bond or lower alkylene;

Y is lower alkylene or lower alkylidene; and n is an integer of 0 or 1; or its pharmaceutically acceptable salt.

2. The compound of claim 1, wherein

R¹ and R² are each alkyl or alkenyl,

R³ is hydrogen, lower alkyl, hydroxy(lower)alkyl or phenyl(lower)alkyl,

R⁴ is carboxy or carboxy(lower)alkyl,

X is bond or lower alkylene, and n is an integer of 0.

3. The compound of claim 2, wherein

R¹ and R² are each tetradecyl, 12-methyltridecyl, pentadecyl or 8-heptadecenyl,

R³ is hydrogen, isopropyl, hydroxymethyl or benzyl,

R⁴ is carboxy, carboxymethyl or carboxypropyl, and

X is bond or methylene.

4. The compound of claim 1, wherein

R¹ and R² are each alkyl or alkenyl,

R³ is hydroxy(lower)alkyl, imidazolyl(lower)alkyl, indolyl(lower)alkyl, phenyl(lower)alkyl, hydroxyphenyl(lower)alkyl or phenyl(lower)alkoxy phenyl(lower)alkyl, R⁴ is carboxy or lower alkoxycarbonyl, X is bond or lower alkylene, Y is lower alkylene or lower alkylidene, and n is an integer of 1.

5. The compound of claim 4, wherein

R¹ and R² are each propyl, pentyl, undecyl, tetradecyl, pentadecyl, 11-methyldodecyl, 12-methyltridecyl, 12-methyl-3-tridecenyl or 8-heptadecenyl, R³ is hydroxymethyl, 1-hydroxyethyl, imidazolylmethyl, indolylmethyl, benzyl, hydroxybenzyl or benzyloxybenzyl, R⁴ is carboxy or methoxycarbonyl, X is bond or methylene, and Y is methylene, ethylene, butylene, ethylidene or butylidene.

6. An immunological pharmaceutical composition comprising an immunologically effective amount of a compound of claim 1 in association with a pharmaceutically acceptable, substantially non-toxic carrier or excipient.

* * * * *